United States Patent
Boutros

(10) Patent No.: US 10,252,021 B2
(45) Date of Patent: Apr. 9, 2019

(54) BI-DIRECTIONAL OXYGENATION APPARATUS FOR A NON-INTUBATED PATIENT

(71) Applicant: Sean Boutros, Houston, TX (US)

(72) Inventor: Sean Boutros, Houston, TX (US)

(*) Notice: Subject to any disclaimer, the term of this patent is extended or adjusted under 35 U.S.C. 154(b) by 0 days.

(21) Appl. No.: 15/837,532

(22) Filed: Dec. 11, 2017

(65) Prior Publication Data

US 2019/0046757 A1   Feb. 14, 2019

Related U.S. Application Data

(63) Continuation-in-part of application No. 15/672,530, filed on Aug. 9, 2017.

(51) Int. Cl.
  *A61M 16/20* (2006.01)
  *A63B 23/18* (2006.01)

(52) U.S. Cl.
  CPC .......... *A61M 16/201* (2014.02); *A63B 23/18* (2013.01)

(58) Field of Classification Search
  CPC .. A61M 16/20; A61M 16/201; A61M 16/206; A61M 16/207; A61M 16/208; A61M 16/209; A63B 23/18
  USPC ............ 128/207.14, 207.15, 207.16, 207.18; 482/13
  See application file for complete search history.

(56) References Cited

U.S. PATENT DOCUMENTS

| | | | |
|---|---|---|---|
| 7,025,060 B1* | 4/2006 | Nicholson | A62B 23/06 128/206.17 |
| 8,177,689 B2* | 5/2012 | Rutten | A63B 21/00069 482/13 |
| 9,560,887 B2* | 2/2017 | Folkvord | A41D 13/11 |
| 2007/0277832 A1* | 12/2007 | Doshi | A61M 15/08 128/207.18 |

* cited by examiner

*Primary Examiner* — Jan Christopher Merene
*Assistant Examiner* — Elliot S Ruddie
(74) *Attorney, Agent, or Firm* — Dale J. Ream

(57) ABSTRACT

A self-administered oxygenation apparatus for increasing pressure within a non-intubated patient's lungs and thereby increasing an amount of oxygen in the non-intubated patient's blood when operated by the patient includes a mouthpiece, a vent member, and a resistance member. The mouthpiece includes an external portion defining a center orifice through which the patient selectively inhales and exhales air. The vent member includes a continuous side wall fixedly coupled to the external portion of the mouthpiece and defining an interior area in fluid communication with the center orifice. The resistance member is positioned between the interior area of the vent member and the mouthpiece, the resistance member having a flexible construction configured to fold inwardly upon inhalation so as to allow ambient air inhaled by the patient to pass thereby without resistance and having a perforated construction configured to decrease the flow of air exhaled by the patient.

15 Claims, 11 Drawing Sheets

BI-DIRECTIONAL OXYGENATION APPARATUS FOR A NON-INTUBATED PATIENT

REFERENCE TO RELATED APPLICATIONS

This application claims the benefit of non-provisional patent application U.S. Ser. No. 15/672,530 filed Aug. 9, 2017 titled Bi-Directional Oxygenation Apparatus For A Non-Intubated Patient and which is incorporated herein by reference.

BACKGROUND OF THE INVENTION

This invention relates generally to medical equipment intended to increase oxygenation of the blood of a patient who has insufficient pressure in the lungs following exhalation.

Patients in respiratory distress are often hospitalized and, sometimes, require invasive treatment such as intubation and being connected to a machine that both inhales and exhales for them. An electrical breathing machine may be incorporated to generate the mechanics of breathing. The patient in such cases may be unable to inhale or exhale on his own, or at least efficiently. In such instances, doctors may desire respiratory treatments intended to increase the oxygenation of the patient's blood by increasing pressure in the patient's airway.

However, there are patients and even athletes that have non-critical respiratory ailments or conditions that could benefit from increasing the pressure within their airway and, as a result, increasing the oxygenation of their blood. Such individuals are not intubated and do not require a breathing machine to either inhale ambient air or exhale air from their lungs. Putting positive pressure on the lungs of an otherwise unassisted breathing patient or user, such as by resisting normal exhalation, would enhance the oxygenation of the patient's blood and improve his breathing capacity or efficiency.

Although presumably effective for its intended use, the current method of treating a dangerously distressed patient with a full ventilator and intubated patient is undesirable for a patient that is not intubated and not being treated on a full ventilator setup. Stated another way, it would be desirable for a patient capable of inhaling and exhaling on his own to have a bi-directional oxygenation apparatus that allows the patient to inhale air through his mouth and then to exhale through his mouth with mechanical resistance being given to the exhalation, whereby to increase the pressure on the airway, expand any collapsed alveoli in the lungs and, as a result, increase oxygenation of the blood. In addition, it would be desirable to have a bi-directional oxygenation apparatus having a mouthpiece.

SUMMARY OF THE INVENTION

A self-administered oxygenation apparatus according to the present invention for increasing pressure within a non-intubated patient's lungs and thereby increasing an amount of oxygen in the non-intubated patient's blood when operated by the patient includes a mouthpiece, a vent member, and a resistance member. The mouthpiece includes an external portion defining a center orifice through which the patient selectively inhales and exhales air. The vent member includes a continuous side wall fixedly coupled to the external portion of the mouthpiece and defining an interior area in fluid communication with the center orifice. The resistance member is positioned between the interior area of the vent member and the mouthpiece, the resistance member having a flexible construction configured to fold inwardly upon inhalation so as to allow ambient air inhaled by the patient to pass thereby without resistance and having a perforated construction for decreasing the airflow of exhalation and thereby increasing the pressure inside the airway.

Therefore, a general object of this invention is to provide a bi-directional oxygenation apparatus for a patient that includes a mouthpiece that enables the patient to both inhale and exhale air through his mouth.

Another object of this invention is to provide a bi-directional oxygenation apparatus, as aforesaid, that includes a resistance portion that provides resistance to exhaled air so as to expand the patient's airway and increase oxygenation of the patient's blood.

Still another object of this invention is to provide a bi-directional oxygenation apparatus, as aforesaid, in which inhaled air causes the resistance member to fold inwardly toward the mouthpiece so that inhaled air is allowed to pass without resistance.

Yet another object of this invention is to provide a bi-directional oxygenation apparatus, as aforesaid, in which the resistance member includes perforations that decrease a flow of air that is passing outwardly therethrough during exhalation.

A further object of this invention is to provide a bi-directional oxygenation apparatus, as aforesaid, in which mechanical resistance to exhaled air expands any collapsed alveoli in the patient's lungs.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 4a is an end view of the bi-directional oxygenation apparatus as in FIG. 1;

FIG. 4b is a sectional view taken along line 4b-4b of FIG. 4a;

FIG. 8b is a sectional view taken along line 8b-8b of FIG. 8a;

FIG. 13b is a sectional view taken along line 13b-13b of FIG. 13a;

DESCRIPTION OF THE PREFERRED EMBODIMENT

Figure 1:
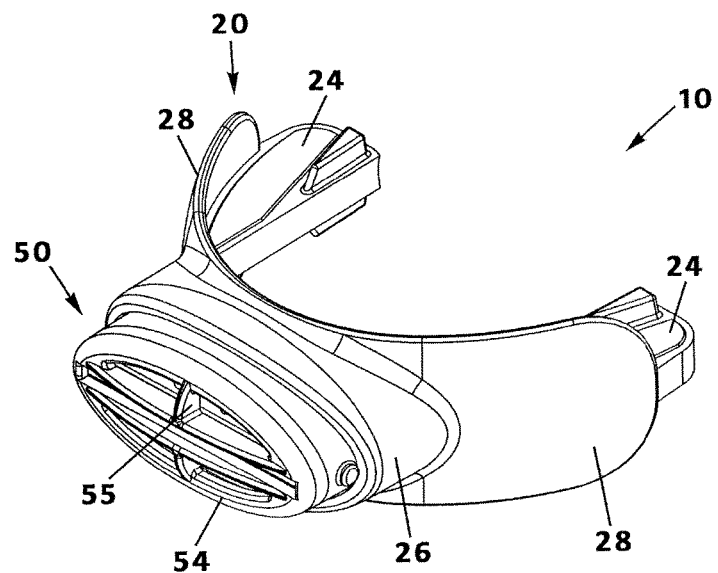
FIG. 1 is a perspective view of a bi-directional oxygenation apparatus according to one embodiment of the present invention.

A bi-directional oxygenation apparatus for a patient according to a preferred embodiment will now be described with reference to FIGS. 1 to 16 of the accompanying drawings. The bi-directional oxygenation apparatus 10 includes a mouthpiece 20 having an external portion 26, a resistance member 30 for regulating inhalation and exhalation resistance, and a vent member 50. As will be described in greater detail later, the vent member 50 may also be referred to as a grill or port through which ambient air is inhaled into the device and patient air is exhaled.

It is understood that references herein to a patient refer to a patient who is not intubated or being treated on a complete respiratory system that essentially inhales and exhales for the patient. Rather, the present invention is for use by a non-intubated patient who is able to inhale and exhale on his own while yet being in need of improved and increased oxygenation of his blood. For instance, an athlete or rehabilitation patient may use the present invention to utilize his own inhalation and exhalation of air to expand his lungs and increase oxygenation of his blood.

The bi-directional oxygenation apparatus 10 includes a mouthpiece 20 that includes an intraoral portion 21 configured for placement inside a patient's mouth and an external portion 26 coupled to the intraoral portion 21 and configured to remain outside the patient's mouth. In its simplest form, the intraoral portion 21 has structures similar to those of a football mouthpiece that may be gripped in between the teeth of a football player. For instance, the mouthpiece 20 may include left and right grip members 24 spaced apart laterally within a horizontal plane or arranged in a bowed configuration complementary to the bowed configuration of a patient's teeth so as to be gripped by the patient's teeth during use (FIG. 1b).

Further, the mouthpiece 20 includes a mouth shield 28 that is positioned intermediate the intraoral portion and the external portion 26. The mouth shield 28 may have a generally hemispherical shape configuration and be both configured and positioned to press against the lips and cheeks of the patient when the intraoral portion 21 is taken into the patient's mouth. The external portion 26 of the mouthpiece 20 defines a central orifice 27 through which air may be inhaled and exhaled by a patient as will be described in further detail below. It may be seen that the intraoral portion 21 and external portion 26 define the central orifice 27 in combination or in communication with one another (FIG. 1b).

In an embodiment of the present invention, the external portion 26 is situated intermediate the vent member 50 and the mouthpiece 20 and provides the structures that make the invention operate efficiently. Specifically, the external portion 26 may have a continuous side wall arranged in an oval shaped configuration although a combination of walls arranged in a rectangular, circular, or irregular configuration would also work. The continuous side wall of the external portion 26 defines a hollow interior space open on both front and rear ends in communication with the central orifice 27 of the mouthpiece 20 and with an open interior area of the vent member 50. In other words, the external portion 26 is essentially a pass through component through which ambient or processed air is inhaled by the patient and through which air from the patient's lungs is exhaled. Preferably, the external portion 26 may have a singular or integrated construction with the mouthpiece 20 and be considered to be the front or forward-most structure of the mouthpiece 20.

Figures 4A, 4B:
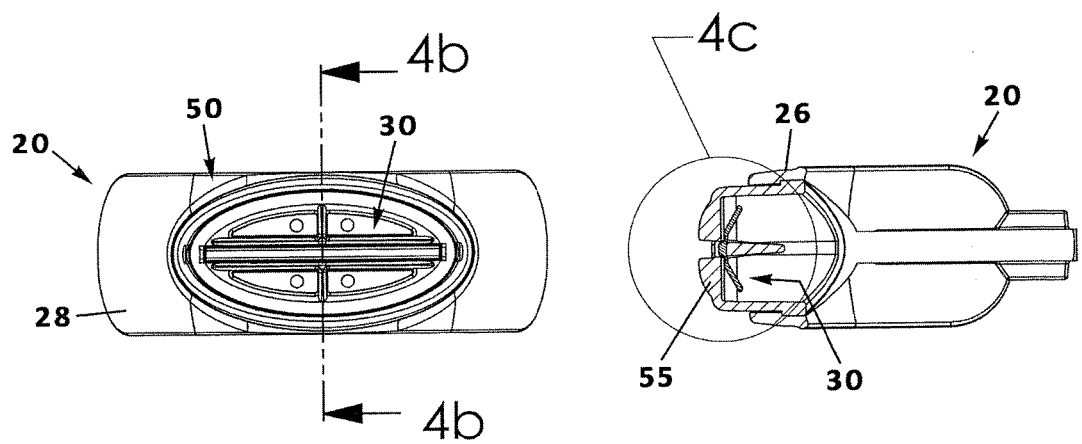
Figure 4C:
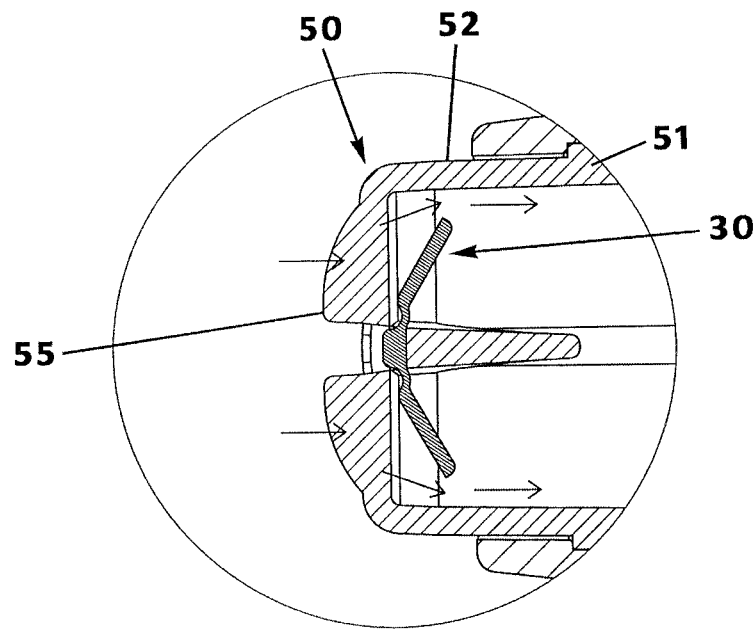
FIG. 4c is an isolated view on an enlarged scale taken from FIG. 4b, illustrated with the resistance member in a folded configuration allowing inhalation without resistance and shown with unnumbered airflow arrows.

The vent member 50 may have a mounting portion 51 having a diameter slightly smaller than a diameter of the central orifice 27 of the external portion 26 of the mouthpiece 20 so as to be slidably received therein in a tight friction fit arrangement. More particularly, the vent member 50 may include a shape configuration complementary to that of the external portion 26 for coupling in a snap-fit arrangement (FIG. 4c). In embodiments (not shown), the vent member 50 may have a unitary construction with the external portion 26 of the mouthpiece 20 such that the vent member 50 is actually connected directly to the mouthpiece 20.

The vent member 50 is the outermost component of the oxygenation apparatus 10 and is the component through which ambient air is inhaled into the mouthpiece 20 and through which air from a user's lungs is finally exhausted when exhaled. Now more particularly, the vent member 50 includes a continuous side wall 52 that defines an interior area in fluid communication with the central orifice 27 defined by the mouthpiece 20. The vent member 50 may include an end shield 54 configured to partially block access to the interior space while still allowing inhalation or exhalation of air therethrough as will be described in more detail below. The end shield 54 may be configured as a grill or grate having one or more support members 55 arranged in a crisscross pattern. As will be described in more detail later, the support member 55 are configured to act as a "stop" or barrier against which upper and lower sections of the resistance member 30 will bear against when resisting exhaled air.

Now, more specifically, the resistance member 30 may have a flexible construction and is mounted inside the interior spaced of the vent member 50 (FIG. 1 to 4d) or, alternatively, in the external portion 26 of the mouthpiece 20. In any case, the resistance member 30 is positioned intermediate the vent member 50 and the external portion 26 of the mouthpiece 20 so that inhaled and exhaled air must pass through or around the resistance member 30, respectively.

Figure 4D:
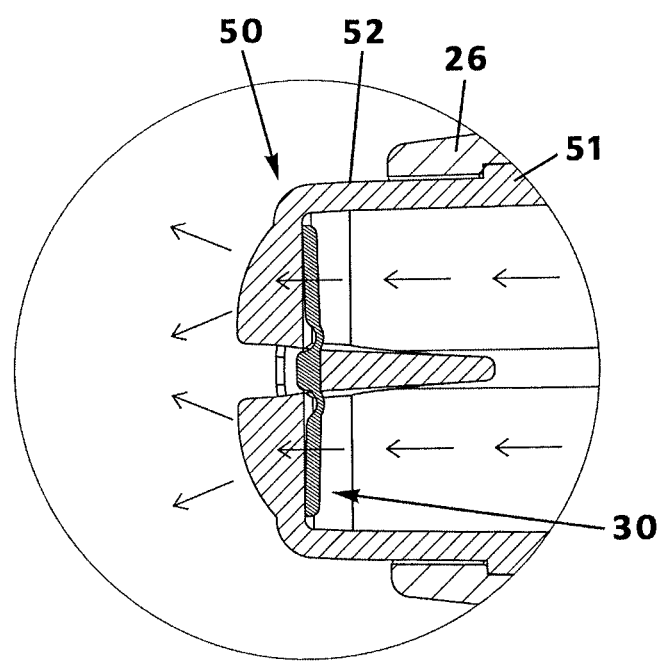
FIG. 4d is an isolated view on an enlarged scale taken from FIG. 4b, illustrated with the resistance member in an unfolded configuration blocking a portion of exhaled air and shown with unnumbered airflow arrows.
Figure 5:
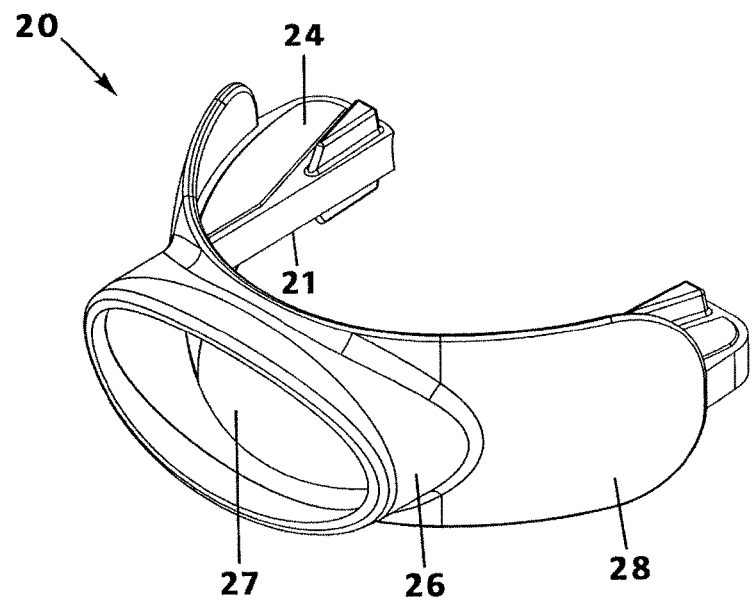
FIG. 5 is an isolated perspective view of the mouthpiece removed from the bi-directional oxygenation apparatus for clarity.
Figure 6:
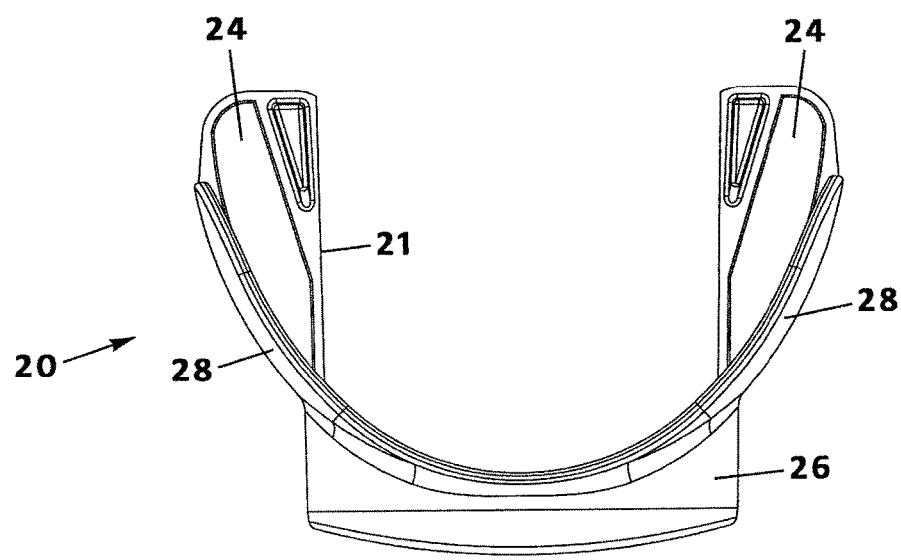
FIG. 6 is a top view of the mouthpiece as in FIG. 5.
Figure 7:
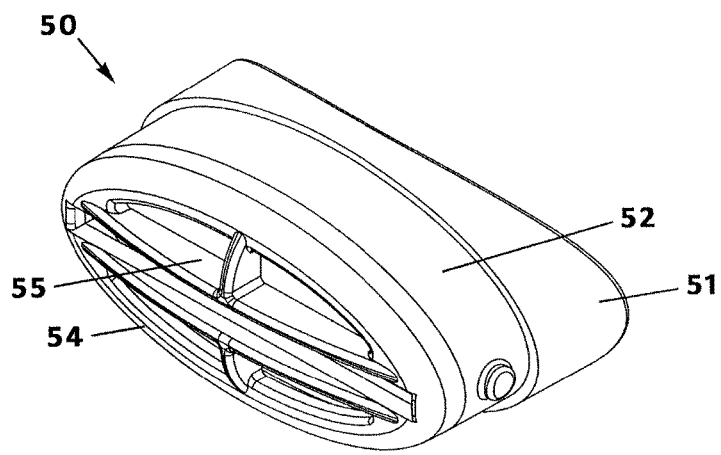
FIG. 7 is an isolated perspective view of the vent member removed from the bi-directional oxygenation apparatus for clarity.
Figure 8A:
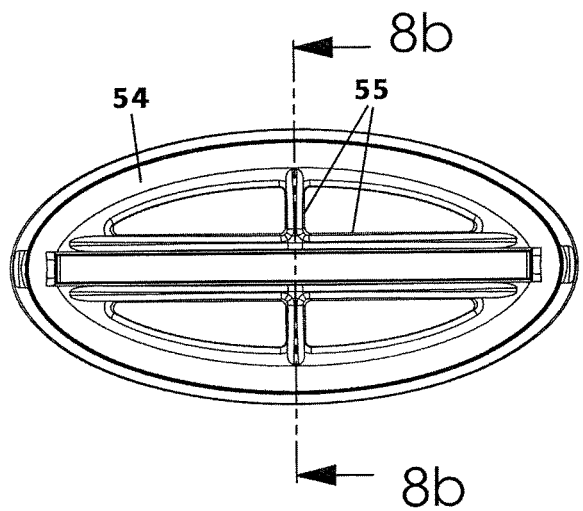
FIG. 8a is an end view of the vent member as in FIG. 7.
Figure 8B:
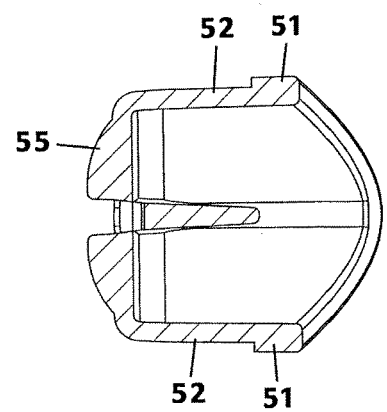
Figure 9:
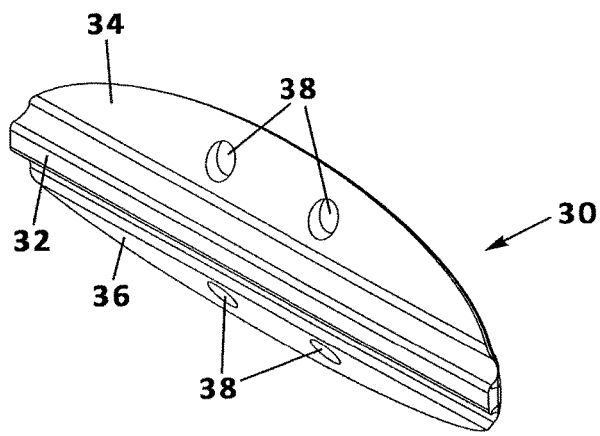
FIG. 9 is an isolated perspective view of the resistance member removed from the bi-directional oxygenation apparatus for clarity.
Figure 10A:
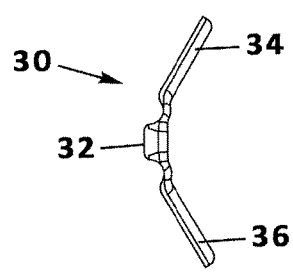
FIG. 10a is a side view of the resistance member as in FIG. 9, illustrated in a folded configuration during inhalation.
Figure 10B:
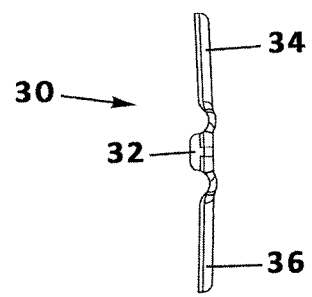
FIG. 10b is a side view of the resistance member as in FIG. 9, illustrated in a unfolded configuration during exhalation.
Figure 11:
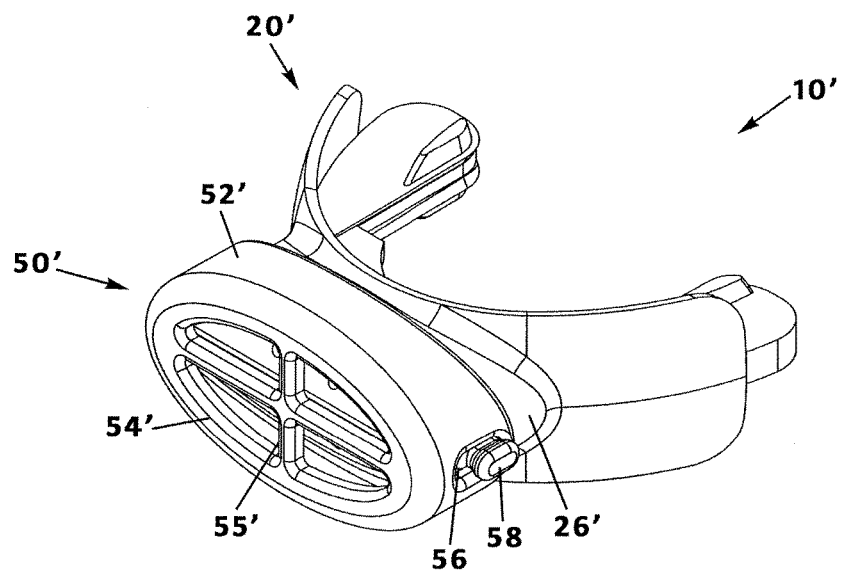
FIG. 11 is a perspective view of a bi-directional oxygenation apparatus according to another embodiment of the present invention.
Figure 12:
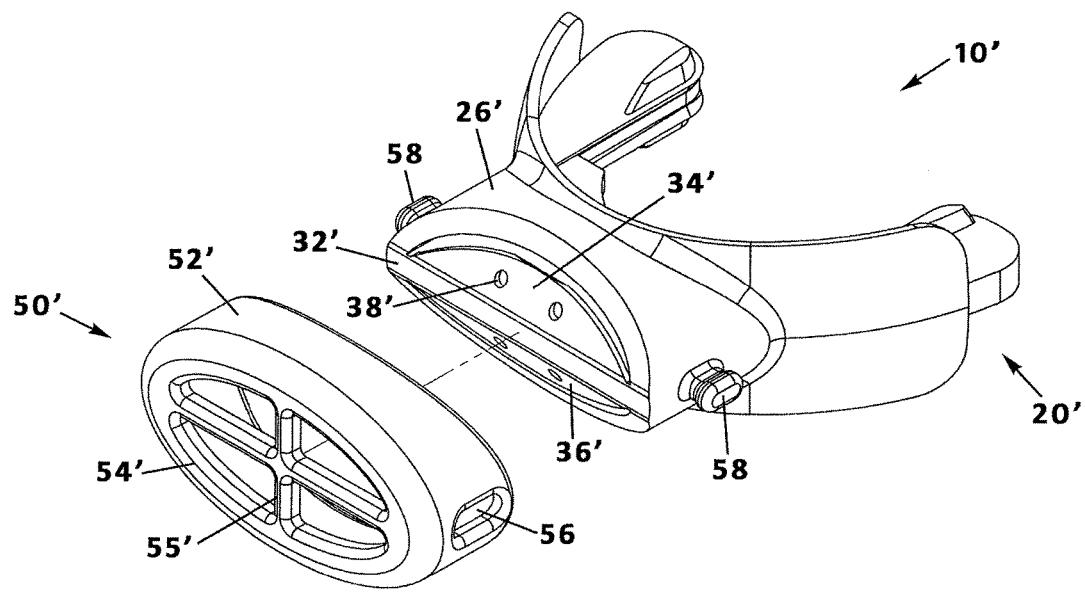
FIG. 12 is an exploded view of the bi-directional oxygenation apparatus as in FIG. 12.
Figure 13A:
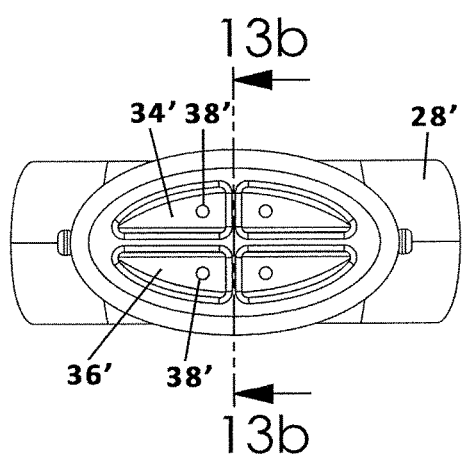
FIG. 13a is an end view of the bi-directional oxygenation apparatus as in FIG. 11.
Figure 13B:
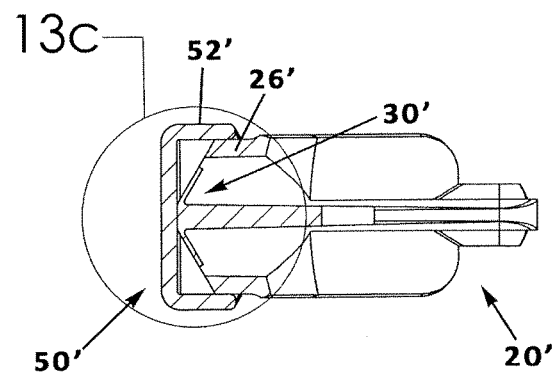
Figure 13C:
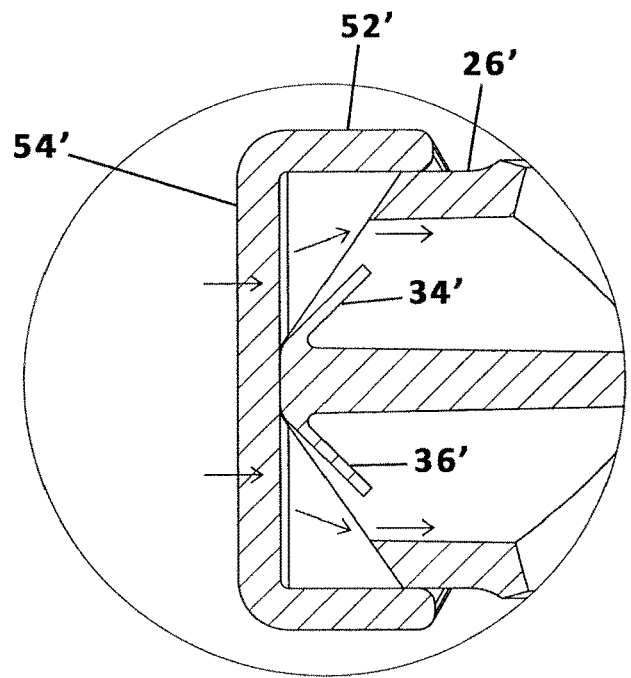
FIG. 13c is an isolated view on an enlarged scale taken from FIG. 13b, illustrated with the resistance member in a folded configuration allowing inhalation without resistance and shown with unnumbered airflow arrows.
Figure 13D:
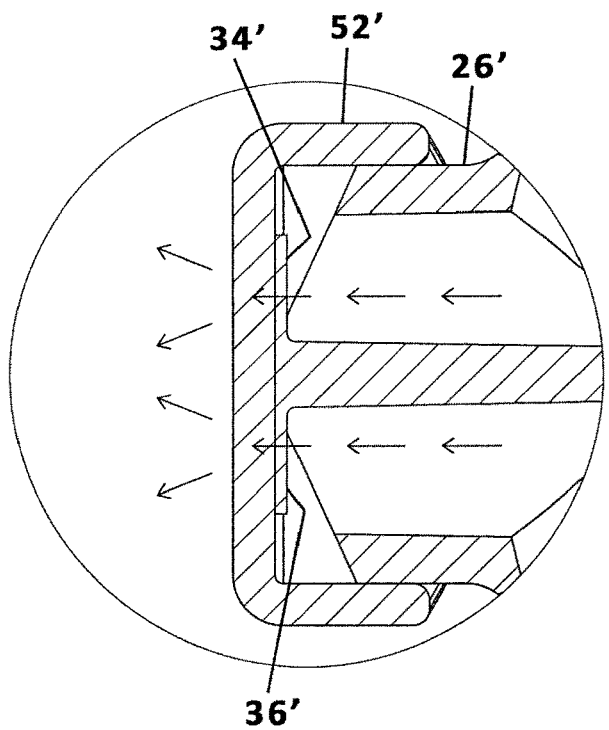
FIG. 13d is an isolated view on an enlarged scale taken from FIG. 13b, illustrated with the resistance member in an unfolded configuration blocking a portion of exhaled air and shown with unnumbered airflow arrows.
Figure 14:
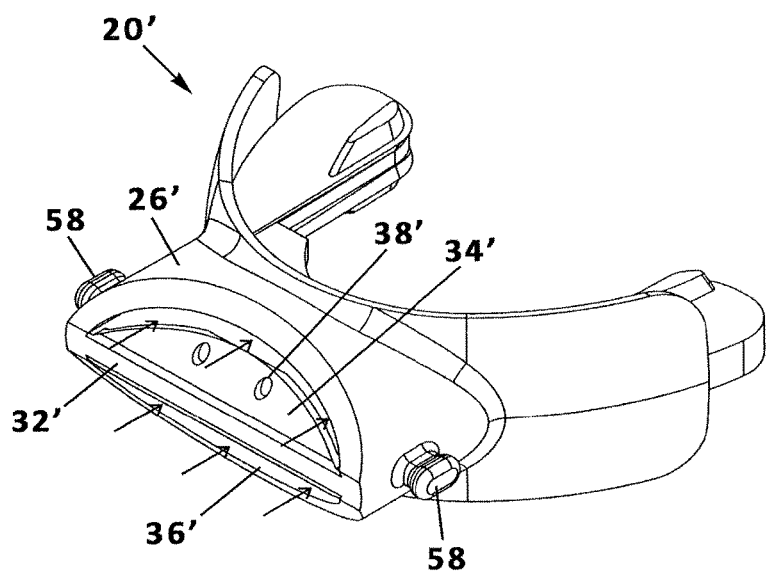
FIG. 14 is an isolated perspective view of the mouthpiece of FIG. 12, illustrated with the resistance member in a folded configuration.

The resistance member 30 includes an upper section 34 and lower section 36 coupled together along a center section 32 that defines a linear axis about which the upper and lower sections pivot. In an embodiment, the resistance member 30 may have a singular or unitary construction having a central line of weakness between the upper and lower sections and about which the sections may pivot. It should be appreciated that FIGS. 4c and 4d are illustrated with unnumbered arrows indicating the direction and flow of air relative to respective sections of the resistance member. More particularly, the upper and lower sections are constructed so as to bow inwardly in the direction of the mouthpiece 20 when air is inhaled such that inhaled air passes over and under the upper section 34 and lower section 36 without resistance (FIG. 4c). Further, air is drawn in between respective support members 55 of the vent member 50 as a user inhales using the mouthpiece 20, the flow of inhaled air causing the upper and lower sections of the resistance member 30 to fold in the direction of the inhaled air. Preferably, the resistance member 30 is positioned immediately adjacent the support members 55 of the vent member.

Further, opposite ends of the center section 32 may be attached to an inner surface of the side wall 52 of the vent member 50 so that the resistance member 30 will not become dislodged or move out of its intended position. Alternatively, the center section 32 may be coupled to respective support members 55 of the vent member 50, such as to a horizontal support member. By contrast, peripheral edges of the upper section 34 and lower section 36 are not fixedly attached to the walls or support members of the vent member 50 and are free to move according to inhaled or exhaled air flow as will be described below.

Regarding exhalation, the resistance member 30 is configured so as to bow and in a direction away from the mouthpiece 20 and toward the support members 55 of the vent member 50 when air is exhaled through the central orifice 27. If not otherwise stopped by a tangible structure, the resistance member 30 would define a convex configuration when pushed by exhaled air. However, in the preferred embodiment, the resistance member 30 is positioned adjacent the support members 55 such that exhaled air urges the upper section 34 and lower section 36 to a planar configuration that bears against and blocks the open end of the vent member 50 (FIG. 4d). At this configuration, the resistance member 30 establishes an airtight seal within the vent member 50 such that exhaled air is blocked—unless another opening is provided.

Figure 2:
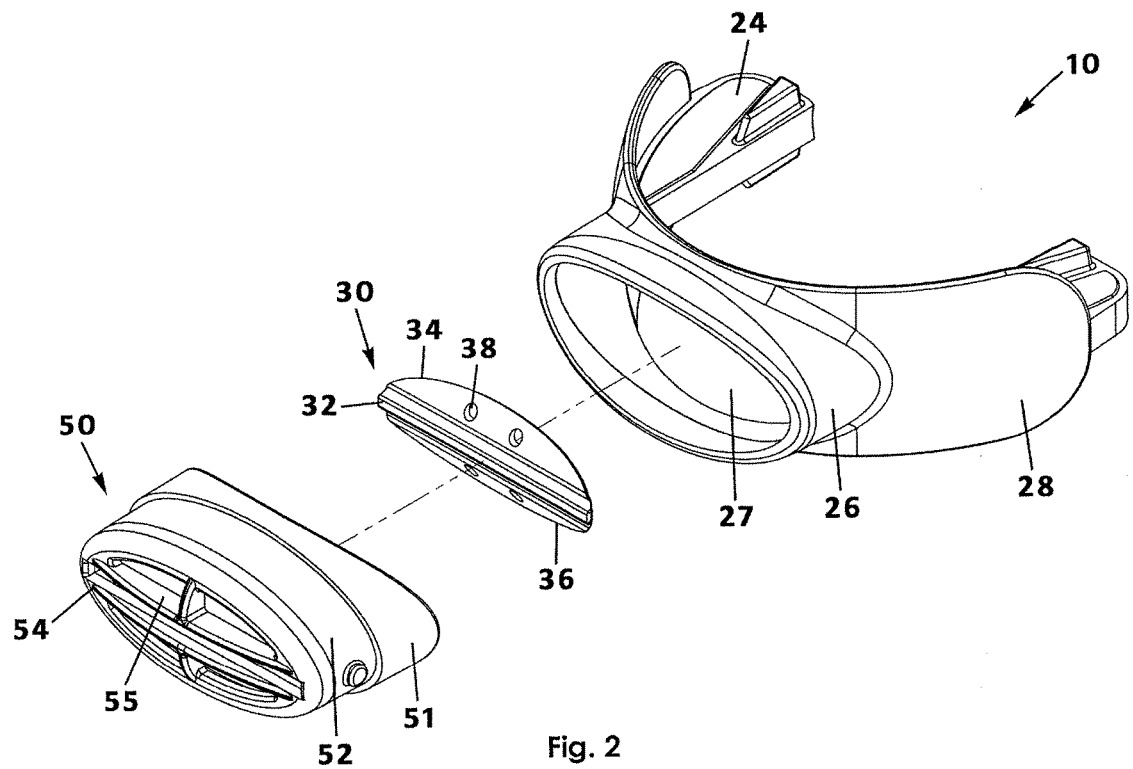
FIG. 2 is an exploded view of the bi-directional oxygenation apparatus as in FIG. 1.
Figure 3:
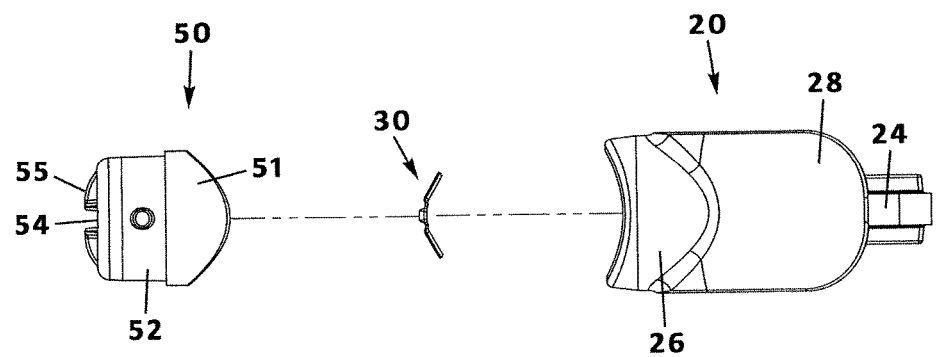
FIG. 3 is a top view of the bi-directional oxygenation apparatus as in FIG. 2.

In this regard, the upper and lower sections of the resistance member 30 define one or more openings 38 through which a predetermined quantity of exhaled air is allowed to pass outside and away from the vent member 50 (FIG. 2). The size of each opening or the quantity of openings defines the degree or amount of resistance to exhalation, pressure on the airway, and oxygenation of the user's blood.

A bi-directional oxygenation apparatus 10' according to a related embodiment of the present invention is substantially similar to the embodiment except as specifically described below with similar structures identified with primed numerals even if not recited again below. Specifically, the vent member 50' may be attached to an exterior of the exterior portion 26' of the mouthpiece 20' (FIGS. 11 to 15). More particularly, the side wall 52' of the vent member 50' includes a diameter larger than that of the external portion 26' of the mouthpiece 20' so as to be slidably coupled to an outside surface of the external portion 26. In the instant embodiment, the side wall 52' of the vent member 50' defines opposed mounting apertures 56. Correspondingly, the exterior portion 26' of the mouthpiece 20' includes at least a pair of mounting flanges 58, each mounting flange 58 having a shape and size configuration appropriate to be received in respective mounting apertures 56. Accordingly, the vent member 50' may be removably coupled to an exterior of the exterior portion 26' of the mouthpiece 20' in a friction fit or snap-fit arrangement.

Figure 15:
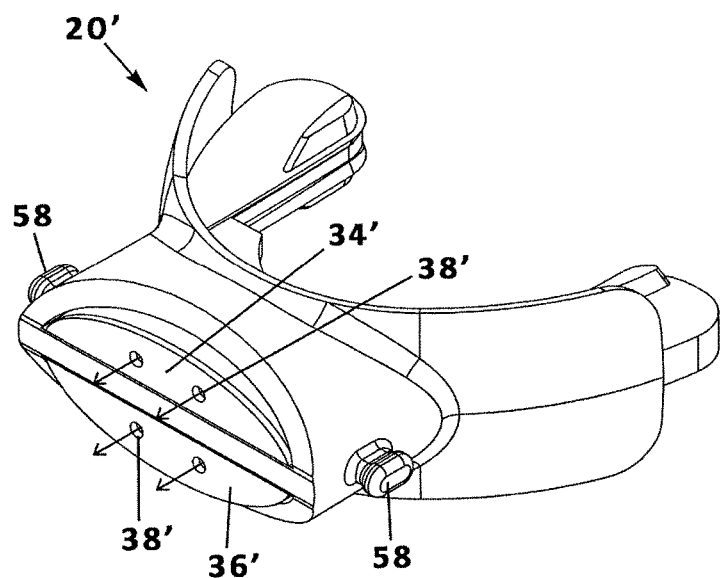
FIG. 15 is an isolated perspective view of the mouthpiece of FIG. 12, illustrated with the resistance member in a unfolded configuration.

Further, a restraining member 30' may be coupled to the open end of the external portion 26'. Specifically, opposed ends of the center section 32' of the restraining member 30' may be attached or integrally constructed to opposed sides of the external portion 26' of the mouthpiece 20', the restraining member 30' having an upper section 34' and lower section 36' that function in the same manner as described above. FIGS. 13c, 13d, 14, and 15 are illustrated with unnumbered arrows that indicate the direction of inhaled or exhaled air and the corresponding action of the respective sections of the resistance member 30'. For instance, FIG. 15 illustrates exhaled air passing outwardly through openings 38' in the upper 34' and lower 36' sections. In addition, the side wall 52' of the vent member 50' has a dimension that enables the restraining member 30' to be positioned adjacent the support members 55' of the end shield 54' of the vent member 50' to, again, maintain operation as first described above.

Figure 16:
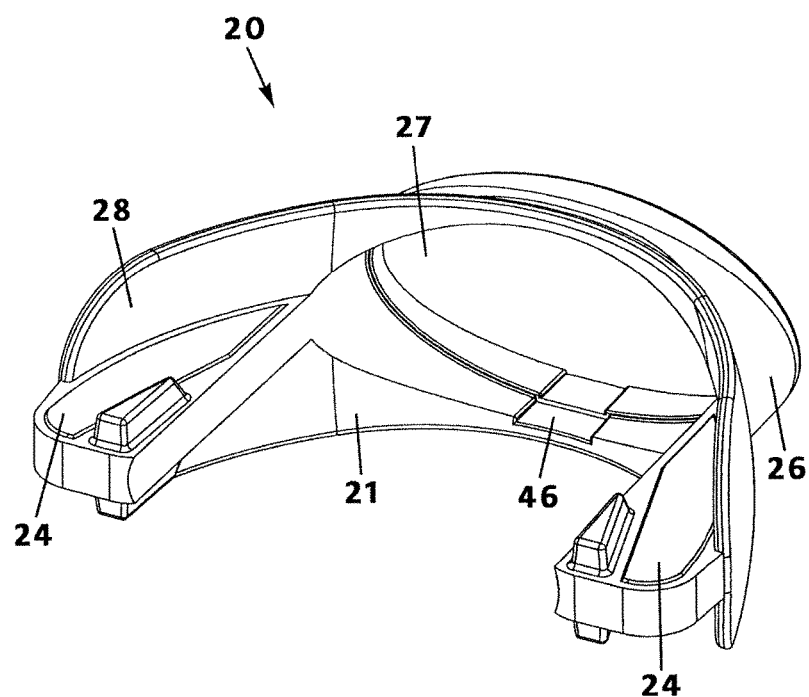
FIG. 16 is as perspective view of the mouthpiece illustrating that, in an embodiment, a saliva collection area is included.

In another aspect, a lower or bottom interior surface of the external portion 26 may be recessed to define a collection area 46 (shown only in FIG. 16). More particularly, the collection area 46 is configured to collect saliva that may come through the central orifice 27 as part of the air exhaled by a patient. The collection area 46 may include a rearwardly and downwardly angled surface such that collected saliva is returned to the mouthpiece and, ultimately, to the mouth of the patient. This structure is important so that moisture is not accumulated on the surface of the restraining member 30.

In use, a non-intubated patient desiring to enhance the oxygenation of his blood by expansion of his lung capacity can inhale and exhale through the football style mouthpiece 20 of the bi-directional oxygenation apparatus 10 as described above. Ambient air may be inhaled without any resistance as inhalation causes the sections of the resistance member 30 to fold inwardly. Then, the inhaled air may be exhaled through the mouthpiece, the exhaled air causing the resistance member 30 to be sealed against the grill of the vent member 50 which provides mechanical resistance as exhaled air must pass through the openings 38. With each cycle of inhalation and then exhalation, the lungs of the patient are expanded, more oxygen is retained at the conclusion of an exhalation and, as a result, more oxygen is received into the blood (i.e. oxygenation occurs).

Accordingly, the present invention allows oxygenation enhancement therapy to be available to a non-intubated patient.

It is understood that while certain forms of this invention have been illustrated and described, it is not limited thereto except insofar as such limitations are included in the following claims and allowable functional equivalents thereof.

The invention claimed is:

1. A self-administered oxygenation apparatus for increasing pressure within a non-intubated patient's lungs and thereby expanding collapsed alveoli and thereby increasing an amount of oxygen in patient's blood when operated singly by the non-intubated patient who is capable of unassisted inhalation and exhalation, said self-administered oxygenation apparatus comprising:
   a mouthpiece having an external portion defining a center orifice through which the patient selectively inhales and exhales air;
   a vent member having a continuous side wall coupled to said external portion of said mouthpiece and defining an interior area in fluid communication with said center orifice;
   wherein said vent member includes an end shield operable to partially block access to the interior space while still allowing inhalation or exhalation of air therethrough;
   a resistance member positioned between said interior area of said vent member and said mouthpiece, said resistance member having a flexible construction for allowing ambient air inhaled by the patient to pass thereby without resistance and having a perforated construction for decreasing a flow of air exhaled by the patient;
   wherein said resistance member includes:
   a center section having a linear configuration;
   an upper section pivotally coupled to an upper edge of said center section, said upper section flexibly operable for pivotally folding away from said end shield of said support member and toward said mouthpiece when air is inhaled and pivotally folding toward and bearing against said end shield of said support member and sealing against an inner surface of said side wall of said vent member when air is exhaled, said end shield being a stop against the unfolding of said upper section;
   a lower section pivotally coupled to a lower edge of said center section, said lower section pivotally folding away from said end shield of said support member and toward said mouthpiece when air is inhaled and pivotally folding toward and bearing against said end shield of said support member and sealing against an inner surface of said side wall of said vent member when air is exhaled, said end shield being a stop against the unfolding of said upper section;
   wherein said upper section and said lower section include a perforated construction for decreasing a flow of air exhaled by the patient when said resistance member is folded outwardly against said end shield;
   wherein said resistance member is moved by an inhalation of air from said neutral configuration to a folded configuration at which said upper and lower sections are folded away from said end shield;
   wherein said resistance member is moved by an exhalation of air from said neutral configuration to an unfolded configuration at which said upper and lower sections bear against said end shield.

2. The self-administered oxygenation apparatus as in claim 1, wherein:
   said upper section includes a plurality of openings through which air is allowed to pass when said upper section is at said unfolded configuration and when air is directed toward said upper section;
   said lower section includes a plurality of openings through which air is allowed to pass when said lower section is at said unfolded configuration and when air is directed toward said lower section.

3. The self-administered oxygenation apparatus as in claim 1, wherein said resistance member is constructed of silicone.

4. The self-administered oxygenation apparatus as in claim 1, wherein said mouthpiece includes an intraoral portion for placement in the patient's mouth, said intraoral portion being coupled to said external portion and in fluid communication with said center orifice.

5. The self-administered oxygenation apparatus as in claim 4, wherein:
   said intraoral portion of said mouthpiece includes left and right grip members arranged in a bowed configuration and configured for insertion between teeth of the patient;
   said mouthpiece includes a mouth shield intermediate said intraoral portion and said external portion, said mouth shield having a hemispherical shape configuration.

6. The self-administered oxygenation apparatus as in claim 1, wherein an interior surface of said external portion of said mouthpiece defines a collection area that is configured to collect saliva that passes through said central orifice.

7. The self-administered oxygenation apparatus as in claim 6, wherein said collection area has a downwardly angled surface in a direction toward said mouthpiece so as to return collected saliva toward the mouth of the patient.

8. A self-administered oxygenation apparatus for increasing pressure within a non-intubated patient's lungs and thereby increasing an amount of oxygen in the non-intubated patient's blood when operated singly by the non-intubated patient, said self-administered oxygenation apparatus comprising:
   a mouthpiece having an external portion defining a center orifice through which the patient selectively inhales and exhales air;
   a vent member having a continuous side wall fixedly coupled to said external portion of said mouthpiece and defining an interior area in fluid communication with said center orifice;
   wherein said vent member includes an end shield operable to partially block access to the interior space while still allowing inhalation or exhalation of air therethrough;
   a resistance member positioned between said interior area of said vent member and said mouthpiece, said resistance member comprising:
   a center section having a linear configuration extending between opposed ends of said resistance member;
   an upper section pivotally coupled to an upper edge of said center section, said upper section pivotally folding away from said end shield of said support member and toward said mouthpiece when air is inhaled and pivotally folding toward and bearing against said end shield of said support member and sealing against an inner surface of said side wall of said vent member when air is exhaled, said end shield being a stop against the unfolding of said upper section;
   a lower section pivotally coupled to a lower edge of said center section, said lower section pivotally folding away from said end shield of said support member and toward said mouthpiece when air is inhaled and pivotally folding toward and bearing against said end shield of said support member and sealing against an inner surface of said side wall of said vent member when air is exhaled, said end shield being a stop against the unfolding of said upper section;
   wherein said upper section and said lower section include a perforated construction for decreasing a flow of air exhaled by the patient when said resistance member is folded outwardly against said end shield.

9. The self-administered oxygenation apparatus as in claim 8, wherein said flexible construction of said resistance member is selectively movable between an inwardly folded configuration allowing the ambient air to pass thereover from said vent member to said central orifice of said mouthpiece without any resistance and an unfolded configuration allowing a first portion of air exhaled by the patient to pass through said perforated construction while not allowing a second portion of air exhaled from the patient to pass through said perforated construction.

10. The self-administered oxygenation apparatus as in claim 8, wherein:
said upper section includes an opening through which air is allowed to pass when said upper section is at said unfolded configuration and when air is exhaled by the patient;
said lower section includes an opening through which air is allowed to pass when said lower section is at said unfolded configuration and when air is exhaled by the patient.

11. The self-administered oxygenation apparatus as in claim 8, wherein said resistance member is constructed of silicone.

12. The self-administered oxygenation apparatus as in claim 8, wherein said vent member includes an end shield having a plurality of support members partially blocking access to said interior area thereof but allowing air to be inhaled or exhaled therethrough.

13. The self-administered oxygenation apparatus as in claim 8, wherein said mouthpiece includes an intraoral portion for placement in the patient's mouth, said intraoral portion being coupled to said external portion and in fluid communication with said center orifice.

14. The self-administered oxygenation apparatus as in claim 13, wherein:
said intraoral portion of said mouthpiece includes left and right grip members arranged in a bowed configuration and configured for insertion between teeth of the patient;
said mouthpiece includes a mouth shield intermediate said intraoral portion and said external portion, said mouth shield having a hemispherical shape configuration.

15. A self-administered oxygenation apparatus for increasing pressure within a non-intubated patient's lungs and thereby expanding collapsed alveoli and thereby increasing an amount of oxygen in patient's blood when operated singly by the non-intubated patient who is capable of unassisted inhalation and exhalation, said self-administered oxygenation apparatus comprising:
a mouthpiece having an external portion defining a center orifice through which the patient selectively inhales and exhales air;
a vent member having a continuous side wall coupled to said external portion of said mouthpiece and defining an interior area in fluid communication with said center orifice;
wherein said vent member includes an end shield operable to partially block access to the interior space while still allowing inhalation or exhalation of air therethrough;
a resistance member positioned between said interior area of said vent member and said mouthpiece, said resistance member having a flexible construction for allowing ambient air inhaled by the patient to pass thereby without resistance and having a perforated construction for decreasing a flow of air exhaled by the patient;
wherein said resistance member includes:
a center section having a linear configuration;
an upper section pivotally coupled to an upper edge of said center section, said upper section flexibly operable for pivotally folding away from said end shield of said support member and toward said mouthpiece when air is inhaled and pivotally folding toward and bearing against said end shield of said support member and sealing against an inner surface of said side wall of said vent member when air is exhaled, said end shield being a stop against the unfolding of said upper section;
a lower section pivotally coupled to a lower edge of said center section, said lower section pivotally folding away from said end shield of said support member and toward said mouthpiece when air is inhaled and pivotally folding toward and bearing against said end shield of said support member and sealing against an inner surface of said side wall of said vent member when air is exhaled, said end shield being a stop against the unfolding of said upper section;
wherein said upper section and said lower section include a perforated construction for decreasing a flow of air exhaled by the patient when said resistance member is folded outwardly against said end shield;
wherein said resistance member is moved by an inhalation of air from said neutral configuration to a folded configuration at which said upper and lower sections are folded away from said end shield;
wherein said resistance member is moved by an exhalation of air from said neutral configuration to an unfolded configuration at which said upper and lower sections bear against said end shield wherein an interior surface of said external portion of said mouthpiece defines a collection area that is configured to collect saliva that passes through said central orifice, said collection area having a downwardly angled surface in a direction toward said mouthpiece so as to return collected saliva toward the mouth of the patient.

* * * * *